United States Patent [19]
Maciejewski

[11] Patent Number: 5,177,997
[45] Date of Patent: Jan. 12, 1993

[54] DYNAMIC TEST APPARATUS FOR ELECTRO-RHEOLOGICAL FLUIDS

[75] Inventor: Wendell C. Maciejewski, Salem, Conn.

[73] Assignee: The United States of America as represented by the Secretary of the Navy, Washington, D.C.

[21] Appl. No.: 762,818

[22] Filed: Sep. 16, 1991

[51] Int. Cl.$^5$ ............................................. G01N 11/10
[52] U.S. Cl. .................................................... 73/54.24
[58] Field of Search ................. 73/54.24, 54.01, 54.23, 73/54.31, 54.32, 54.34, 54.37

[56] References Cited

U.S. PATENT DOCUMENTS 3,194,064  7/1965  Miles ............................. 73/54.24 X
4,763,512  8/1988  Taylor ........................... 73/54.24 X Primary Examiner—Hezron E. Williams
Assistant Examiner—Joseph W. Roskos
Attorney, Agent, or Firm—Michael J. McGowan; Prithvi C. Lall; Michael F. Oglo

[57] ABSTRACT

A device is disclosed for determining the dynamic mechanical properties, specifically, G*, G', G", and Tan δ, of an electrorheological (ER) fluid as a function of frequency, voltage and temperature. This is accomplished by using the device in conjunction with a suitable driving and environmental control apparatus. An inner tubular electrode, coaxial with an outer tubular electrode, is oscillated along their common longitudinal axis at frequencies in a range of approximately 5 Hz to approximately 1,000 Hz while the spacing between the electrodes is maintained substantially constant at all opposed portions thereof. A power source provides an electrical field encompassing the inner and outer electrodes and the gap therebetween, and the assoicated driving and environmental control apparatus is operated for measuring the effort required to move the second electrode relative to said first electrode when the ER fluid is received between said inner and outer electrodes. Such measured effort is a function, respectively, of the characteristics of the ER fluid, the rate of oscillation of said second electrode, the strength of the electrical field, and the temperature of the ER fluid.

9 Claims, 1 Drawing Sheet

5,177,997

DYNAMIC TEST APPARATUS FOR ELECTRO-RHEOLOGICAL FLUIDS

STATEMENT OF GOVERNMENT INTEREST

The invention described herein may be manufactured and used by or for the Government of the U.S. of America for governmental purposes without the payment of any royalties thereon or therefor.

BACKGROUND OF THE INVENTION (1) Field of the Invention

The present invention relates to apparatus for determining the dynamic mechanical properties of an electro-rheological (ER) fluid as a function of frequency, voltage, and temperature. The measured properties can then be used to characterize the effectiveness and behavior of the ER fluids for various engineering applications.

(2) Description of the Prior Art

Most ER fluid test methods do not allow for property characterization as a function of high frequencies or temperature. They may be limited to low frequency static testing. There has been limited dynamic testing up to 200 Hz using a flexural beam apparatus. This technique has disadvantages in that it must be fabricated by sandwiching the fluid between two metal plates that will act as the electrodes and sealing all the edges with a leak proof sealant. This technique is difficult, time consuming and messy.

A number of patented constructions typify the prior art. For example, U.S. Pat. No. 4,437,337 to Fenrick discloses a viscoelastometer for measuring a viscoelastic effect in a liquid. A liquid sample cup, in association with a pneumatic cylinder, is moved at a selected rate between an upper and lower position. A rigid member is immersed in the liquid when the sample cup is in the upper position. As the cup moves toward its lower position, the liquid forms a filament between the rigid member and the surface of the liquid. As the rigid member moves away from the liquid surface, the liquid relaxes and separates from the rigid member as a function of the viscosity and elasticity of the fluid.

In another instance, U.S. Pat. No. 4,648,263 to Deysarkar et al discloses a centering support attachment for a viscometer which has a rotating head placed in a stationary container of liquid being tested.

U.S. Pat. No. 4,862,735 to Williams et al discloses a viscometer which, in operation, oscillates a probe within a container filled with a fluid specimen. Strain gages are mounted on a lever connected to the probe for measuring shear forces experienced by the probe a it oscillates.

It was with knowledge of the prior art as just described that the present invention was conceived and has now been reduced to practice.

SUMMARY OF THE INVENTION

The present invention relates to a device for determining the dynamic mechanical properties, specifically, $G^*$, $G'$, $G''$, and Tan $\delta$, of an electro-rheological (ER) fluid as a function of frequency, voltage and temperature. This is accomplished by using the device in conjunction with a suitable driving and environmental control apparatus. An inner tubular electrode, coaxial with an outer tubular electrode, is oscillated along their common longitudinal axis at frequencies in a range of approximately 5 Hz to approximately 1,000 Hz while the spacing between the electrodes is maintained substantially constant at all peripheral locations. A power source provides an electrical field encompassing the inner and outer electrodes and the associated driving and environmental control apparatus is operated for measuring the effort required to move the second electrode relative to said first electrode when the ER fluid is received between said inner and outer electrodes. Such measured effort is a function, respectively, of the characteristics of the ER fluid, the rate of oscillation of said second electrode, the strength of the electrical field, and the temperature of the ER fluid.

Alternative materials may be chosen for various conduction, insulation or chemical compatibility reasons. The materials are dependent on the fluid used, voltage applied, and apparatus they are connected to. Variations in size and electrode spacing can be easily accommodated, depending upon the driving apparatus used.

A general purpose and object of the invention is to provide a device able to perform dynamic material measurements of ER fluids over a broad range of temperatures and frequencies and to much higher levels than heretofore employed.

Other advantages associated with this invention are that it is economical, simple, easy to manufacture, and easy to clean and operate. The size of the invention may be varied depending on the apparatus used to drive it and any variety of materials could be used to build it.

Other and further features, advantages, and benefits of the invention will become apparent from the following description taken in conjunction with the following drawings. It is to be understood that the foregoing general description and the following detailed description are exemplary and explanatory but are not to be restrictive of the invention. The accompanying drawings which are incorporated in and constitute a part of this invention, illustrate one of the embodiments of the invention, and, together with the description, serve to explain the principles of the invention in general terms. Like numerals refer to like parts throughout the disclosure.

DETAILED DESCRIPTION OF THE PREFERRED EMBODIMENT

Figure 1:
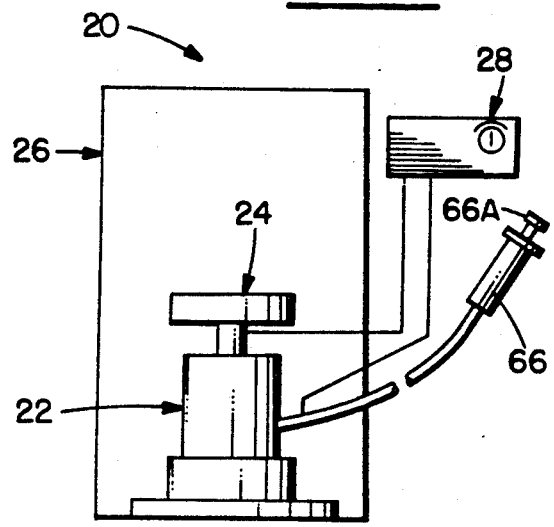
FIG. 1 is a diagrammatic view illustrating the system of the invention, the system being shown with presence of a syringe plunger which is used in introducing into the system the fluid to undergo testing, but it is to be appreciated that this syringe plunger must be removed during system operation.

Turn now to the drawings and, initially, to FIG. 1 which diagrammatically illustrates a system 20 for measuring the dynamic mechanical properties of a electrorheological (ER) fluid. The dynamic mechanical properties of a material are defined as follows:

G': the real component of the shear or storage modulus;

G": the imaginary component of the shear modulus, also referred to as the loss modulus;

G*: complex shear modulus, that is, the square root of the sum of the squares of the real and imaginary components $[(G')^2+(G'')^2]^{\frac{1}{2}}$; and Tan $\delta = G''/G'$: referred to as the loss factor.

The dynamic properties are of particular interest when studying polymers such as elastomers and are a function of both time and temperature.

When studying the dynamic properties of a material, testing performed over a broad frequency range is desirable. Often times an investigator seeks to isolate vibrations and noises that can occur at high frequency levels. As a result, the broader the range of frequencies that can studied, the better equipped the investigator is to design appropriate isolation. The system of the invention possesses a capability in this regard which far surpasses known systems.

The system 20 includes a base assembly 22, a plunger assembly 24 operated by a suitable controlling instrument 26, and a suitable electronic power supply 28.

Figure 3:
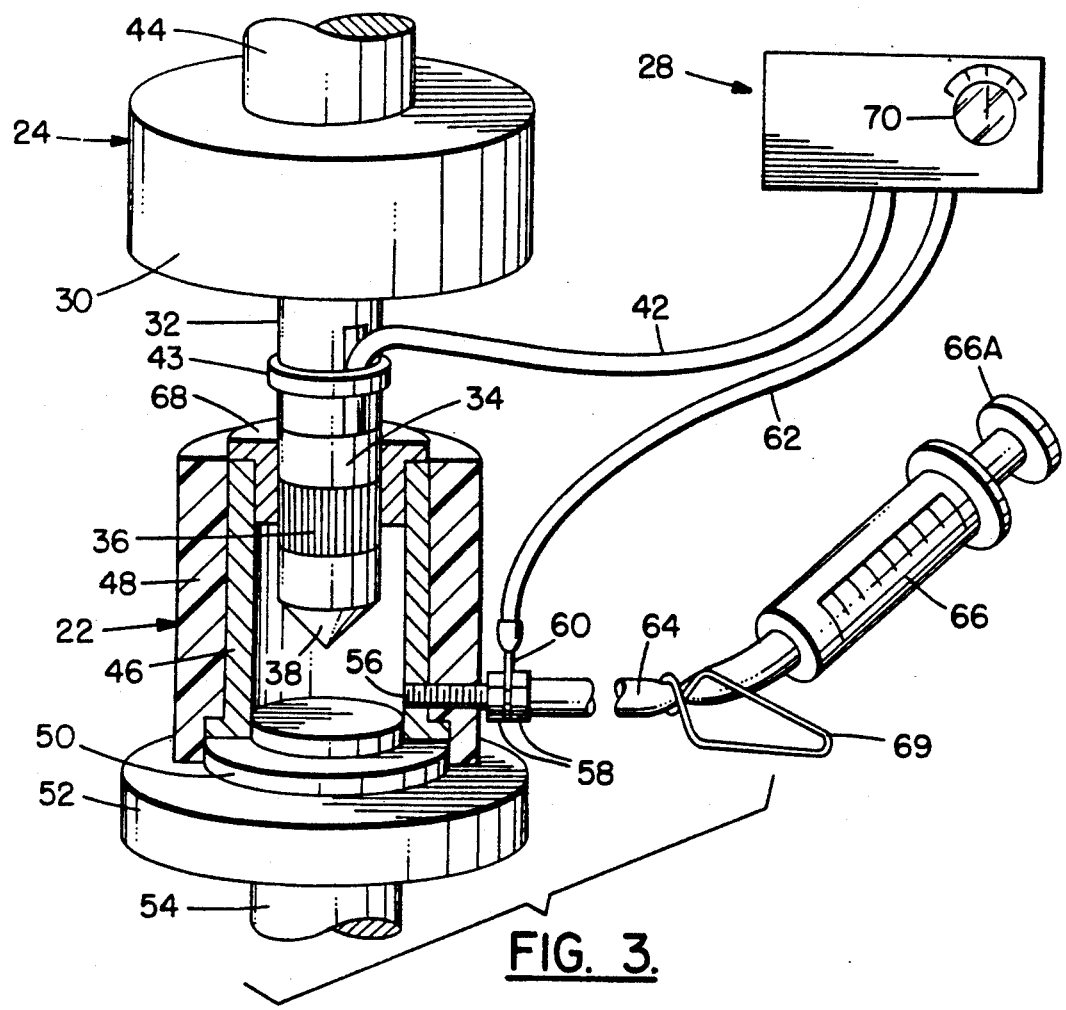
FIG. 3 is a perspective view, with parts partly cut away and shown in section, of apparatus embodying the present invention, the apparatus being (i) shown with presence of a bushing member which is used as a fixture in the fabrication of the apparatus, but it is to be appreciated that this member must be removed during system operation, and (ii) shown with presence of a syringe plunger which is used in introducing into the apparatus the fluid to undergo testing, but it is to be understood that the syringe plunger must be removed during system operation.
Figure 2:
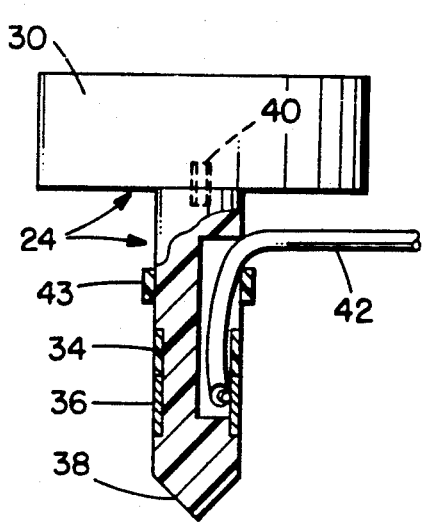
FIG. 2 is a detail side elevation view, with parts partially shown in section, of one component of the system illustrated in FIG. 1.

Referring now to FIGS. 2 and 3, the plunger assembly 24 includes an instrument interface adapter 30 and a stem assembly. The stem assembly is comprised of a top extension adapter 32, a nonconducting adapter 34, a metal electrode ring 36 and an insulating tip 38. To rigidly connect the plunger assembly to the test apparatus, the instrument interface adapter serves as the coupling link to the instrument test head 44. The plunger assembly is fastened to the instrument interface adapter by a metal screw 40 that is threaded into tapped holes in both the instrument interface adapter 30 and the top extension adapter 32. The top extension adapter is machined to accept a press fit of a male end of the nonconducting adapter 34. The other end of the nonconducting adapter 34 is machined to accept a press fit of the electrode ring 36 The insulating tip 38 extends beyond the electrode ring 36.

There is a space machined out of the top extension adapter 32 and non-conducting adapter 34 such that when the electrode ring 36 is assembled, its surface is flush with that of the insulating adapter and tip. Provision must be made in the stem and extension adapters to allow a wire 42 to be electrically connected to the inside of the electrode ring and be guided up and out to a power supply 28.

The system 20 provides for the plunger assembly 24 to be placed into a container of fluid. The wire is held in position with a wire tie 43. It is suitably mounted to a moving test head 44 (FIG. 3) of the controlling instrument 26 which may be, for example, a Metravib Viscoanalyzer, Model No. 545, manufactured by Metravib Instruments of Limonest, France. The base assembly 22 is basically a receptacle for the ER fluid. It consists of a hollow metal insert or outer electrode 46 insulated by a nonconducting canister 48, plug 50, and base 52 integral with a stationary adapter 54. The canister is glued along its bottom edge to the base.

A threaded screw 56 with a hole through it is welded to the side of the outer electrode 46 such that it provides a path of electrical conduction to the outer electrode. The hole extends through the screw and the wall of the outer electrode. The canister must allow sufficient clearance for the screw to extend through its side, but must also have a construction and arrangement to provide ample insulation between the inner and the outer electrode. There are two nuts 58 placed on the threaded portion of the screw to provide a locking system for a wire connector 60 for a wire 62 to the power supply 28.

A small diameter plastic hose 64 is then slipped over the screw 56 and clamped, if necessary, to provide a leak proof path for the fluid from a reservoir 66. The reservoir 66 must be open to the atmosphere to prevent a vacuum lock from occurring. For this purpose, a graduated syringe may be used. It provides a measure of the fluid put into the canister and fits onto the plastic hose 64. (The condition of reservoir 66 being open to the atmosphere during operation of system 20 is not evident in FIGS. 1 and 3 because a syringe plunge 66A is shown as present in reservoir 66. However, as will be explained later herein the plunger 66A is removed as a final step of pumping ER fluid into the canister.)

When the base and plunger assemblies 22, 24 are installed in the controlling instrument 26, they appear as in the cutaway schematic (FIG. 3) or diagrammatic view of FIG. 1. The plunger assembly 24 is lowered into the fluid within the canister 48 until the electrode is positioned some distance below the top of the canister. At this point a critical issue develops. Once in position, the presence of the plunger electrode ring 36 in the canister electrode creates a cylinder of air, or a spacing of size depending on relative sizes of the plunger electrode and canister electrode. This spacing is maintained peripherally constant by means of a bushing 68 received at the upper end of the canister. It is a critical issue because it is across this spacing that the electrical field acts on the fluid. The bushing 68 is used to center the axis of the plunger electrode 36 relative to the outer electrode 46. It is used during set up of the device. Once the canister is properly glued in position and the alignment of all moving components is assured, the bushing is removed. It is not in place during actual operation of the system 20. Therefore the density of the field and strength of the ER fluid are a function of the width of the gap. Using a metering device, in this case the graduated syringe 66 filled with ER fluid, the fluid can be pumped into the canister through the hose, screw, and hole by means of a plunger 66A. It is pumped in until the fluid appears at the top of the canister. The hose is then pinched by means of a resilient clamp 69 to prevent withdrawal of fluid from the canister, and the plunger is then gently removed. The open syringe with remaining fluid is then reconnected to the hose by removal of clamp 69.

The open syringe is required to prevent the test instrument from creating an incompressible slug of ER fluid trapped below the plunger electrode. If this happens, the measurements become invalid because the electric field is not free to move.

The plunger electrode wire 42 is connected to the DC power supply 28 with variable voltage controls 70. The wire 62 from the screw 56 in the canister 48 is connected to a ground on the power supply. When voltage is applied to the system, an electric field is created in the gap between the plunger electrode and the canister electrode. This voltage effects the fluid by causing suspended particles to preferentially align themselves. The strength of the bond between the particles is a function of the applied voltage level.

The dynamic controlling instrument is then used to vary other parameters. In this case, the instrument 26 is set up and configured to vary the frequency of oscillation and to constrain the displacement of the plunger as well as control the temperature. During operation, the fluid in the annulus between the two electrodes is acted upon by the electric field. The viscosity of that fluid changes in the effected region, becoming stiffer with voltage, frequency and decreasing temperature. The plunger then oscillates vertically, creating a shearing motion on the fluid between the electrodes.

The system measures the stiffness and phase of the entrained fluid as a result of the applied motion. It will be appreciated that by knowing this along with knowing the geometries of the device, one is able to calculate the dynamic shear properties of the fluid.

While a preferred embodiment of the invention has been disclosed in detail, it should be understood by those skilled in the art that various other modifications may be made to the illustrated embodiment without departing from the scope of the invention as described in the specification and defined in the appended claims.

What is claimed is:

1. Apparatus for measuring the dynamic mechanical properties of an electro-rheological (ER) fluid comprising:

a stationary first electrode integral with a receptacle for holding a predetermined volume of an ER fluid to be analyzed, said first electrode having a longitudinal axis and an internal peripheral surface parallel to said longitudinal axis and electrically connected to ground potential;

a second electrode having an outer peripheral surface centrally positioned within said first electrode, said outer peripheral surface being substantially uniformly spaced at all locations from said inner peripheral surface, thereby defining a tubular shaped gap between said first and second electrodes for reception therein of the ER fluid, said second electrode supported for oscillating movement relative to said first electrode along said longitudinal axis;

a source of power for providing an electrical field encompassing said first and second electrodes;

whereby the effort required to move said second electrode relative to said first electrode is a function, respectively, of the characteristics of the ER fluid, the rate of oscillation of said second electrode, the strength of the electrical field, and the temperature of the ER fluid.

2. Measuring apparatus as set forth in claim 1:
    wherein said internal peripheral surface is cylindrical;
    wherein said outer peripheral surface is cylindrical; and
    thereby defining an annular gap therebetween for reception of the ER fluid therein.

3. Measuring apparatus as set forth in claim 1 including:
    a receptacle having a cavity with a cylindrical interior surface;
    wherein said stationary electrode is mounted on said interior surface and has a cylindrical inner surface; and
    wherein said outer peripheral surface is cylindrical;
    thereby defining an annular gap therebetween for reception of the ER fluid therein.

4. Measuring apparatus as set forth in claim 1 including:
    means for selectively delivering a predetermined volume of the ER fluid to the gap between said first and second electrodes.

5. Measuring apparatus as set forth in claim 1 including:
    means for mechanically oscillating said second electrode at selected frequencies in the range of approximately 5 Hz to approximately 1,000 Hz.

6. Measuring apparatus as set forth in claim 1 including:
    drive means for mechanically oscillating said second electrode along said longitudinal axis; and
    a power source for controlling the strength of the electrical field.

7. Measuring apparatus as set forth in claim 1 including a source of ER fluid; and
    delivery means for delivering a predetermined volume of the ER fluid to said receptacle without creating the formation of an incompressible slug thereof which would interfere with movement of the electrical field under oscillation of the second electrode relative to the first electrode.

8. Measuring apparatus as set forth in claim 7:
    wherein said receptacle is elongated and in coaxial relationship with the electrodes and has an open end and a closed end:
    wherein said source of ER fluid includes a graduated syringe and a plunger movably mounted thereon and removable therefrom;
    wherein said delivery means includes;
    conduit means fluidically connecting said syringe to the receptacle at a zone of the receptacle adjacent to the closed end thereof;
    valve means operably associated with said conduit means for selectively controlling the flow of ER fluid from said syringe to the receptacle;
    whereby said valve means can be opened and said plunger can be operated to deliver a predetermined amount of ER fluid into the receptacle, then said valve means can be operated to terminate flow of the ER fluid between said syringe and the receptacle, then said plunger can be removed to obviate effects of the fluid between said syringe and the receptacle acting as an incompressible slug after said valve means is again operated to permit flow of fluid through said conduit means.

9. Apparatus for measuring the dynamic mechanical properties of an ER fluid comprising:
    an outer tubular electrode having a longitudinal axis;
    an inner tubular electrode coaxial with said outer tubular electrode and of such diameter to provide a uniform annular gap between the inner and outer electrodes;
    means for creating an electrical field encompassing said inner and outer tubular electrodes and the annular gap therebetween;
    said inner electrode being oscillatingly movable along said longitudinal axis at frequencies in a range of approximately 5 Hz to approximately 1,000 Hz while maintaining the spacing therebetween substantially constant at all peripheral locations;
    whereby the effort required to move said second electrode relative to said first electrode when the ER fluid is received between said inner and outer electrodes is a function, respectively, of the characteristics of the ER fluid, the rate of oscillation of said second electrode, the strength of the electrical field, and the temperature of the ER fluid.

* * * * *